United States Patent
French et al.

(10) Patent No.: US 10,695,318 B2
(45) Date of Patent: *Jun. 30, 2020

(54) METHODS AND COMPOSITIONS FOR IMPROVING COGNITIVE FUNCTION

(71) Applicant: MARS, Incorporated, McLean, VA (US)

(72) Inventors: Stephen French, Nottingham (GB); Amar P Inamdar, Wodonga (AU); Ian Andrew MacDonald, Nottingham (GB); Susan T Francis, Nottingham (GB)

(73) Assignee: MARS, INCORPORATED, McLean, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/241,373

(22) Filed: Jan. 7, 2019

(65) Prior Publication Data

US 2019/0209518 A1 Jul. 11, 2019

Related U.S. Application Data

(63) Continuation of application No. 15/014,255, filed on Feb. 3, 2016, now Pat. No. 10,201,522, which is a continuation of application No. 11/818,604, filed on Jun. 15, 2007, now Pat. No. 9,283,203.

(60) Provisional application No. 60/813,948, filed on Jun. 15, 2006.

(51) Int. Cl.
| | |
|---|---|
| *A61K 31/353* | (2006.01) |
| *A23L 33/105* | (2016.01) |
| *A23G 1/48* | (2006.01) |
| *A23G 1/56* | (2006.01) |
| *A61K 31/7048* | (2006.01) |

(52) U.S. Cl.
CPC ............ *A61K 31/353* (2013.01); *A23G 1/48* (2013.01); *A23G 1/56* (2013.01); *A23L 33/105* (2016.08); *A61K 31/7048* (2013.01); *A23G 2200/14* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 5,733,797 A | 3/1998 | Yamaha | |
| 9,283,203 B2 | 3/2016 | French | |
| 10,201,522 B2 * | 2/2019 | French | |
| 2002/0086067 A1 | 7/2002 | Choi et al. | |
| 2003/0017998 A1 | 1/2003 | Snow et al. | |
| 2003/0054057 A1 | 3/2003 | Kosuna | |
| 2003/0180406 A1 | 9/2003 | Sies | |
| 2004/0043054 A1 | 3/2004 | Shell et al. | |

FOREIGN PATENT DOCUMENTS

| | | |
|---|---|---|
| WO | 2005/020932 A2 | 3/2005 |
| WO | 2005123096 | 12/2005 |
| WO | 2006126895 A2 | 11/2006 |
| WO | 2007002851 | 1/2007 |

OTHER PUBLICATIONS

Engler, M.B., et al. The emerging role of flavonoid-rich cocoa and chocolate in cardiovascular health and disease; Nutrition Reviews, vol. 64, No. 3, Mar. 2006: 109-118.
Ding, E.L. et al. Chocolate and prevention of cardiovascular disease: as systematic review; Nutr. Metab. {Lond.} Jan. 3, 2006; 3:2.
Rohdewald, P. A review of the French maritime pine bark extract (Pycnogenol), a herbal medication with a diverse clinical pharmacology. International Journal of Clinical Pharmacology and Therapeutics, 40{4}, 2002, 158-168.
Grimm, T. et al. Single and multiple dose pharmacokinetics of maritime pine bark extract (Pycnogenol) after oral administration to healthy volunteers. BMC Clinical Pharmacology, 6(4), 2006.
D'Andrea, G., Fitoterapia, vol. 81, pp. 724-736.
Collie, A., Polyphenols and cognition, AgroFOOD Industry Hi-Tech, Jan.-Feb. 2006, 17(1):XVII-XIX.
Baba, S. et al., Absorption and urinary excretion of (-)-epicatechin after administration of different levels of cocoa powder or (-)-epicatechin in rats., J. Agric. Food Chern. 2001, 49, 6050-6056.
Hannum, S. M. et al., Chocolate: A heart-healthy food? Show me the science!, Nutrition Today, 2002, 37(3): 103-109.
Nang, W-F. et al., A study of the correlation between visual spatial cognitive activities and cerebral blood flow velocity changes in normal young people., Chinese Journal of Clinical Psychology, 2005, 13(1 ):88-90.
Cao et al., Anal Bioanal Chem, 2002, vol. 374, pp. 294-299.
The American Heritage® Medical Dictionary definition of "Executive function", 2009, p. 1 of 1, downloaded from YourDictionary.com on Mar. 11, 2010.
Fisher N.D.L. et al., Cocoa Flavanols and Brain Perfusion, J. Cardiovas. Pharmacol., 47(Suppl. 2):210-214 (2006).
Francis S.T. et al., The Effect of Fiavanol-rich Cocoa on the fMRI Response to a Cognitive Task in Healthy Young People, J. Cardiovas. Pharmacol.,47(Suppl. 2): S215-S220 (2006).
Howes M-J. R et al., Plants with Traditional Uses and Activities, Relevant to the Management of Alzheimer's and Other Cognitive Disorders, Phytotherapy Research, I7: I-I8 (2003).
Alspach G, The Truth is Often Bittersweet . . . Chocolate Does a Heart Good, Critical Care Nurse, 27(1): 11-15 (2007).
Heiss C. et al., Vascular Effects of Cocoa Rich in Flavan-3-ols, JAMA, 290(8): 1030-1031 (2003).

(Continued)

*Primary Examiner* — Savitha M Rao
*Assistant Examiner* — Gregg Polansky
(74) *Attorney, Agent, or Firm* — Nath, Goldberg & Meyer; Joshua B. Goldberg; Scott H. Blackman

(57) ABSTRACT

This invention relates to compositions, and methods of use thereof, for (i) enhancing executive cognitive function(s) (for example, decision making, planning, working memory, multitasking, judgment, numerical problem-solving, reading comprehension), and/or (ii) increasing blood flow in brain vasculature, comprising administering to a subject in need thereof, certain polyphenols such as flavanols, procyanidins, or pharmaceutically acceptable salts or derivatives thereof.

20 Claims, 4 Drawing Sheets

(56) References Cited

OTHER PUBLICATIONS

Youdim K. A., et al., A Possible Emerging Role of Phytochemicals in Improving Age-Related Neurological Dysfunctions: A Multiplicity of Effects, Free Radical Biology & Medicine, 30:583-594 (2001).
Youdim K.A., et al., Flavonoids and the Brain: Interactions at the Blood-Brain Barrier and Their Physiological Effects on the Central Nervous System, Free Radical Biology & Medicine, 37(11): 1683-1693 (2004).
Williamson G. and Manach C., Bioavailability and bioefficacy of polyphenols in humans. II. Review of 93 intervention studies, 2005, Am. J. Clin. Nutr., 81 (suppl):243S-55S.
Unno K. et al., Suppressive effect of green tea catechins on morphologic and functional regression of the brain in aged mice with accelerated senescence (SAMP10), 2004, Experimental Gerontology, 39: 1027-1034.
Haque A. M. et al., Long-term administration of green tea catechins improves spatial cognition learning ability in rats, 2006, J. Nutr., 136:1043-1047.
Choc full of health benefits, News item in: Scottish Daily Record and Sunday Mail Ltd., Jul. 26, 2005.
Research finds flavanols in cocoa may help treat diabetes, strokes and dementia, New item in: PR Newswire US, Market Watch, Nurse week, Jul. 25, 2005.
Watson E., Candy good for you? Mars to probe cocoa benefits, Reuters News, Jul. 25, 2005.
Mastroiacovo, Daniela et al., "Cocoa flavanol consumption improves cognitive function, blood pressure control, and metabolic profile in elderly subjects: the Cocoa Cognition, and Aging (CoCoA) Study—a randomized controlled trial", Am J Clin Nutr, first published ahead of print Dec. 17, 2014 as doi: 10:3945/ajcn.114.092189. print pub: vol. 101(3), pp. 538-548.
Desideri, Giovambattista et al., "Benefits in Cognitive Function, Blood Pressure, and Insulin Resistance Through Cocoa Flavanol Consumption in Elderly Subjects With Mild Cognitive Impairment" The Cocoa, Cognition, and Aging (coCoA) Study, Hypertension Journal of the American Heart Association, published on line Aug. 14, 2012. print pub: vol. 60, pp. 794-801.
Brickman, Adam M et al., "Enhancing dentate gyru function with dietary flavanols improves cognition in older adults", Nature Neuroscience, published on line Oct. 26, 2014. print pub: vol. 17(12), pp. 1798-1803.
Cocoa Polyphenols, (Cambridge Chocolate Technology), Jan. 15, 2005, 2 pages.
Dajas F., et al. "Neuroprotection by flavonoids", Brazilian Journal of Medical and Biological Research, vol. 36, pp. 1613-1620, 2003.
European examination report in corresponding EP application No. 07 809 501.5 dated Sep. 13, 2017.
Wikipedia, "Chess", Wikipedia, downloaded on Feb. 20, 2018 from "en.wikipedia.org/wiki/chess", 22 pages.
Ana Clara Aprotosoaie et al., The Cardiovascular Effects of Cocoa Polyphenols-An Overview, The Cardiovascular Effects of Cocoa Polyphenols-An Overview, Dec. 17, 2016, Diseases 2016, 4, 39, 25 pages.
Barry Callebaut, Barry Callebaut confirms the power of polyphenols in chocolate, Nov. 29, 2005, 6 pages.
Summons to Attend Oral Proceedings Pursuant to Rule 115(1) EPC dated Dec. 11, 2019 corresponding to European Application No. 07809501.5-1109.

\* cited by examiner

Threes Correct

Sevens Errors

RVIP Reaction Time

Mental Fatigue

METHODS AND COMPOSITIONS FOR IMPROVING COGNITIVE FUNCTION

This application claims the benefit, under 35 USC Section 119, of the U.S. Provisional Appl. No. 60/813,948 filed Jun. 15, 2006, the disclosure of which is hereby incorporated herein by reference.

FIELD OF THE INVENTION

The invention relates to compositions, and methods of use thereof, for (i) enhancing executive cognitive functions (for example, decision making, planning, working memory, multitasking, judgment, numerical problem-solving, reading comprehension), and/or (ii) increasing blood flow in brain vasculature, comprising administering to a subject in need thereof, certain polyphenolic compounds described herein.

BACKGROUND OF THE INVENTION

The flavanols and procyanidins have attracted a great deal of attention in the fields of medicine and nutrition due to the wide range of their biological activities (e.g. U.S. Pat. No. 6,297,273). Applicants have now discovered that administration of the compounds recited herein leads to an enhancement of executive cognitive function(s) and/or to an increase in blood flow in brain vasculature.

Magnetic resonance imaging (MRI) is an imaging technique that is based on the principles of nuclear magnetic resonance (NMR), a spectroscopic technique used to obtain microscopic chemical and physical information about molecules. MRI is used primarily in medical settings to produce high quality images of the inside of the human body. MRI systems can also image flowing blood in virtually any part of the body. This allows for studies that show the arterial system in the body, but not the tissue around it. In many cases, the MRI system can do this without a contrast injection, which is required in vascular radiology.

Changes in blood flow and blood oxygenation (collectively known as hemodynamics) in the brain vasculature are known to be closely linked to/accompany neural activity (i.e., brain activity/function). Therefore, brain activity/function can be studied by mapping changes in brain hemodynamics using imaging techniques. Functional Magnetic Resonance Imaging (fMRI) is one such magnetic resonance (MR)-based technique used to determine brain function. It measures changes in brain activity through the blood oxygenation level dependent contrast ("BOLD") effect. The BOLD effect is based on changes in distribution of oxygenated hemoglobin. When brain cells are active they consume oxygen carried by hemoglobin in red blood cells from local capillaries. This oxygen utilization leads to an increase in blood flow to regions of increased brain activity which results in local changes in the relative concentration of oxyhemoglobin and deoxyhemoglobin. Hence, the oxygenation change measured by the BOLD response arises from a complex interplay of increases in cerebral blood flow (CBF), cerebral blood volume (CBV), and cerebral metabolic rate of oxygen consumption ($CMRO_2$). Thus, changes in the BOLD signal are well correlated with changes in blood flow, i.e., an increase in the BOLD response is an indication of increased blood flow which in turn may correspond to increased cognitive function, for example enhanced mental acuity and/or abilities.

Arterial Spin Labeling (ASL) is another non-invasive magnetic resonance (MR)-based imaging technique that provides a physiologically relevant measure of CBF in absolute units (i.e., ml of blood/100 grams of tissue/minute). ASL-based imaging is made possible by the same regional neurovascular coupling that is the basis of BOLD response; however, it provides a quantitative measure of changes in blood flow itself rather than of changes in blood oxygenation.

The use of the above brain imaging techniques (fMRI BOLD response and ASL) has allowed for the invention described herein.

Executive cognitive functions play critical roles in the performance of numerous complex tasks, for example, decision making, planning, working memory, multitasking, judgment, numerical problem-solving, and reading comprehension. Therefore, there is a need in the art for methods of enhancing executive cognitive function(s) and/or for increasing blood flow in the brain.

SUMMARY OF THE INVENTION

This invention relates to compositions, and methods of use thereof, for (i) enhancing executive cognitive function(s), and/or (ii) increasing blood flow in brain vasculature, comprising administering to a subject in need thereof certain polyphenolic compounds described herein.

In one aspect, the invention relates to a composition, such as a pharmaceutical, a food, a food additive, or a dietary supplement comprising the compounds of the invention. The composition may optionally contain an additional cognition-enhancing/improving agent, or may be administered in combination with an additional cognition-enhancing/improving agent. Packaged products containing the above-mentioned compositions and a label and/or instructions for use to enhance/improve mental cognition and/or treat/prevent conditions that are associated with declining mental cognition are also within the scope of the invention.

In a further aspect, the invention relates to method of increasing brain activity (assessed for example by using the fMRI BOLD response) in certain regions of the brain comprising administering the compounds of the invention to a subject in need thereof. Non-limiting examples of such activated brain regions include the right-dorsolateral prefrontal cortex, the parietal cortex, and the anterior cingulate.

In another aspect, the invention relates to a method of increasing blood flow to the brain (measured for example by using ASL) comprising administering the compounds of the invention to a subject in need thereof.

Figure 4A:
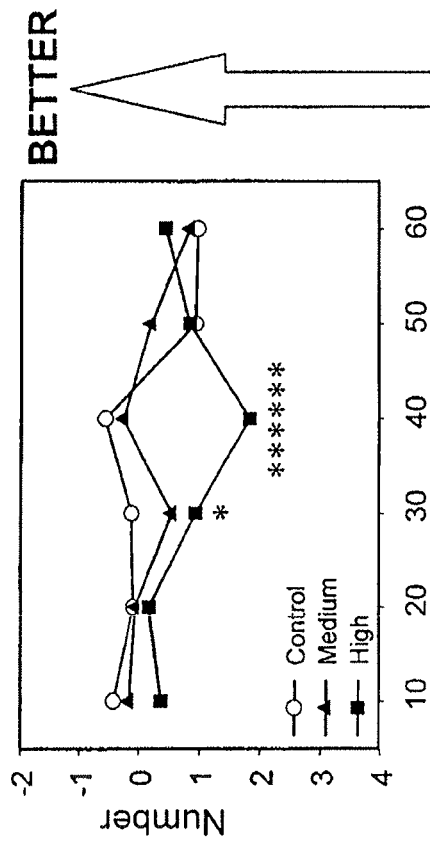
Figure 4B:
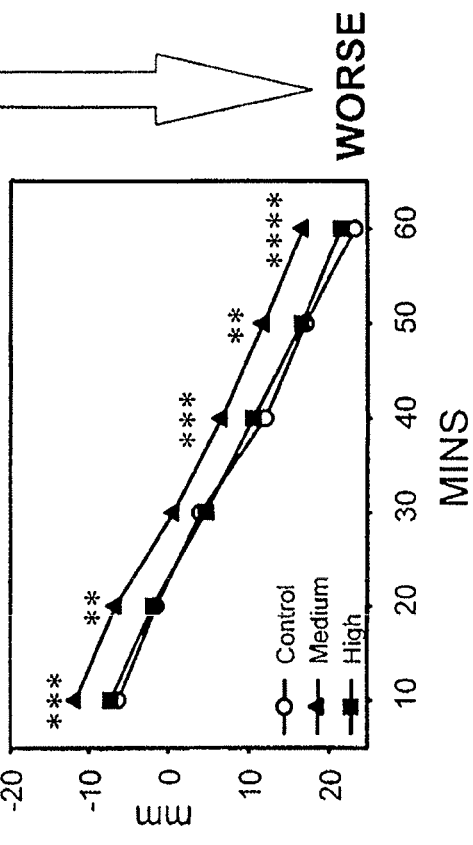
Figure 4C:
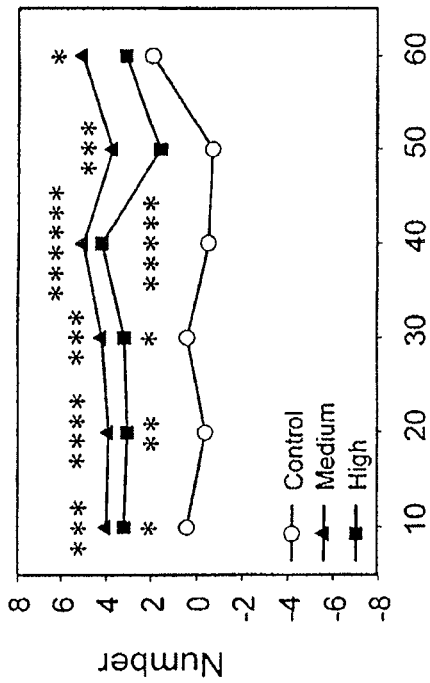

FIG. (4A-4D): shows the effects of a cocoa drink supplemented with flavanols/procyanidins on a "Cognitive Demand Battery" of tests:

FIG. 4A: Threes Correct test;

FIG. 4B: Sevens Error test;

FIG. 4C: Rapid Visual Information Processing Task (RVIP); and

Figure 4D:
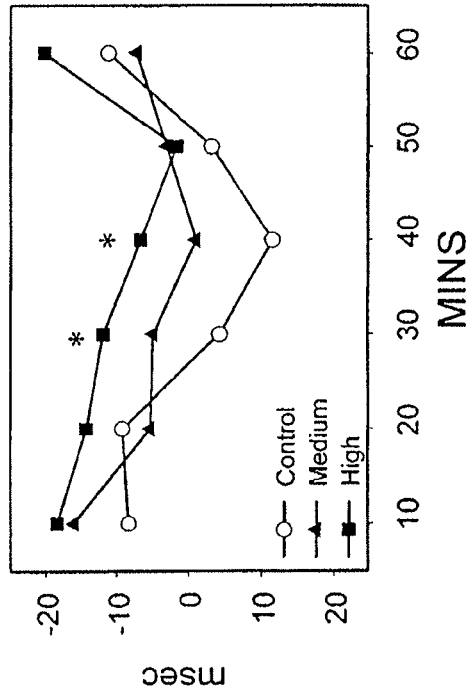

FIG. 4D: Mental fatigue.

DETAILED DESCRIPTION

All patents, patent applications and references cited in this application are hereby incorporated herein by reference. In case of any inconsistency, the present disclosure governs.

The present invention relates to compositions, products, and methods for (i) enhancing executive cognitive function(s), and/or (ii) increasing blood flow in brain vasculature, each comprising administering, to a subject in need thereof, certain polyphenolic compounds described herein. The compounds for use in the present invention include certain flavanols (flavan-3-ols), procyanidins, or pharmaceutically acceptable salts or derivatives thereof. Such compounds, when of natural origin, may be included in the composition in the form of a cocoa component, for example cocoa nibs or fragments thereof, chocolate liquor, cocoa solids (e.g. partially or fully-defatted), cocoa extract or fraction thereof.

As used herein, the term "flavanol" or "flavan-3-ol" refers to a monomer of the following formula:

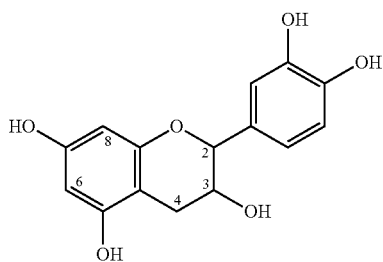 [SMILES: Oc1cc(O)c2c(c1)OC(c1ccc(O)c(O)c1)C(O)C2]

The term "procyanidin" refers to an oligomer of the monomer shown above.

The term "cocoa component" refers to a component derived from cocoa bean, e.g. cocoa nibs and fragments thereof, chocolate liquor, cocoa solids (e.g. partially and fully-defatted cake or powder), flavanol and/or procyanidin-containing cocoa extract or fraction thereof.

In certain embodiments, the present invention relates to a flavanol (e.g. (−)-epicatechin and (+)-catechin), and a composition comprising an effective amount of the flavanol (e.g. (−)-epicatechin and (+)-catechin), or a pharmaceutically acceptable salt or derivative thereof (including oxidation products, methylated derivatives, and glucuronidated derivatives). The derivatives may be prepared as described below.

In other embodiments, the present invention relates to a compound, and a composition comprising an effective amount of the compound, having the following formula An, or a pharmaceutically acceptable salt or derivative thereof (including oxidation products, methylated derivatives, and glucuronidated derivatives):

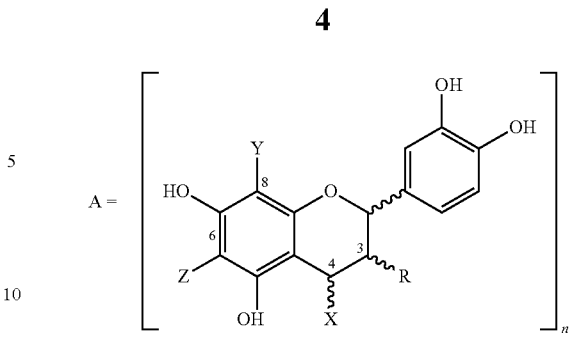

wherein
n is an integer from 2 to 18;
R and X each have either α or stereochemistry;
R is OH or O-sugar or O-gallate;
the substituents of C-4, C-6 and C-8 are X, Z and Y, respectively, and bonding of monomeric units occurs at C-4, C-6 or C-8;
when any C-4, C-6 or C-8 is not bonded to another monomeric unit, X, Y and Z independently are hydrogen or a sugar; and
the sugar is optionally substituted with a phenolic moiety at any position, for instance, via an ester bond.

Monomeric units in the formula An may be bonded via 4---→6a; 4---→6; 4---→8a; and/or 4---→8 linkages. The sugar is preferably a monosaccharide or a disaccharide. The sugar may be selected from the group consisting of glucose, galactose, rhamnose, xylose, and arabinose. The phenolic moiety may be selected from the group consisting of caffeic, cinnamic, coumaric, ferulic, gallic, hydroxybenzoic and sinapic acids. Derivatives may include esters such as the gallate esters; compounds derivatized with a saccharide moiety such as mono- or disaccharide moiety (e.g. -D-glucose), glucuronidated and methylated derivatives, and oxidation products. In some embodiments, ester derivatives are other than esters with gallic acid. Oxidation products may be prepared as disclosed in U.S. Pat. No. 5,554,645, the relevant portions of which are incorporated herein by reference. Esters, for example esters with gallic acid, may be prepared using known esterification reactions, and for example as described in U.S. Pat. No. 6,420,572, the disclosure of which is hereby incorporated herein by reference. Methylated derivatives, such as 3'0-methyl-, 4'0-methyl-, and 3'O,4'0-dimethyl-derivatives may be prepared, for example, as described in Cren-Olive et al., 2002, *J. Chem. Soc. Perkin Trans.* 1, 821-830, and Donovan et al., *Journal of Chromatography* B, 726 (1999) 277-283, the disclosures of which are hereby incorporated herein by reference. Glucuronidated products may be prepared as described in Yu et al, "A novel and effective procedure for the preparation of glucuronides," *Organic Letters*, 2 (16) (2000) 2539-41, and as in Spencer et al, "Contrasting influences of glucuronidation and 0-methylation of epicatechin on hydrogen peroxide-induced cell death in neurons and fibroblasts," *Free Radical Biology and Medicine* 31 (9) (2001) 1139-46, hereby incorporated herein by reference. It should be noted that this disclosure applies to all formulas recited herein.

In another embodiment, the invention relates to a compound, and the composition comprising an effective amount the compound having the formula An, or a pharmaceutically acceptable salt or derivative thereof (including oxidation products, methylated derivatives, and glucuronidated derivatives):

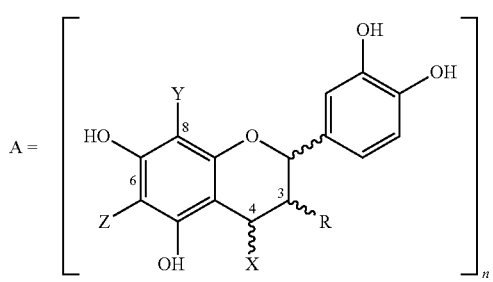

wherein
  n is an integer from 2 to 18;
  R and X each have either α or stereochemistry;
  R is OH;
  the substituents of C-4, C-6 and C-8 are X, Z and Y, respectively, and bonding of monomeric units occurs at C-4, C-6 and C-8; and
  when any C-4, C-6 or C-8 is not bonded to another monomeric unit, X, Y and Z are hydrogen.

Examples of the compounds useful for the products and in the methods of the invention include the compounds of the formula An described herein wherein the integer n is 3 to 18; 2 to 12; 3 to 12; 2 to 5; 4 to 12; 5 to 12; 4 to 10; or 5 to 10. In some embodiments, the integer n is 2 to 4, for example 2 or 3. This disclosure applies to any compound of formula An herein.

Methods of Use

The invention relates to methods of (i) enhancing executive cognitive function(s) and/or (ii) increasing blood flow in brain vasculature.

As used herein, "executive cognitive function" is defined as a higher order cognitive capacity that plays a role in managing (like an "executive") other cognitive functions such as attention, language and memory. Examples of executive cognitive functions include decision-making, multi-tasking, working memory, performance of complex numerical calculations, reading comprehension.

As used herein, "enhancement of cognitive function" is defined as a measurable improvement of at least one of the executive cognitive functions. A person of skill in the art will select the known methods of measuring the improvement of cognitive functions, for example, methods described in the Examples.

As used herein, "decline in cognitive abilities" is defined as a deterioration of cognitive abilities in a healthy subject, for example an elderly/aged subject, i.e., as used herein "decline in cognitive abilities" is not referring to a neurodegenerative condition.

As used herein, a "healthy" subject is one who is not suffering from/has not been diagnosed with a neurodegenerative disease.

As used herein, "increasing blood flow" refers to an increase in the amount of blood delivered to the tissue which may be expressed in terms of milliliters (ml) of blood per 100 ml of tissue per minute. Increasing blood flow in the brain refers to an increase in the volume of blood entering a unit volume of brain per unit of time.

In certain embodiments, the present invention provides (i) a method of enhancing an executive cognitive function and/or (ii) a method of increasing blood flow to brain vasculature, each comprising administering to a mammal (e.g. human) or a veterinary animal in need thereof an effective amount of a flavanol such as epicatechin or catechin (e.g. (−)-epicatechin or (+)-catechin), or a pharmaceutically acceptable salt or derivative thereof (including oxidation products, methylated derivatives, and glucuronidated derivatives).

The term "veterinary animal" refers to any animal cared for, or attended to by, a veterinarian, and includes companion (pet) animals and livestock animals, for example a cat, a dog and a horse (e.g. a race horse).

In certain embodiments, the invention provides (i) a method of enhancing an executive cognitive function and/or (ii) a method of increasing blood flow to brain vasculature, each comprising administering to a mammal (e.g. human) or a veterinary animal in need thereof, a composition comprising an effective amount of a compound having the following formula An, or a pharmaceutically acceptable salt or derivative thereof (including oxidation products, methylated derivatives, and glucuronidated derivatives):

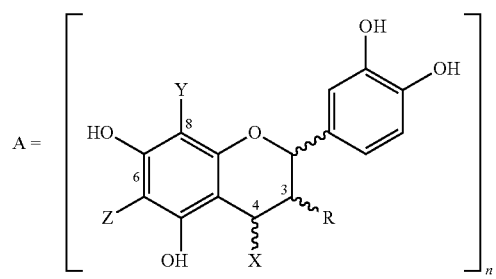

wherein
  n is an integer from 2 to 18;
  R and X each have either α or stereochemistry;
  R is OH or 0-sugar or 0-gallate;
  the substituents of C-4, C-6 and C-8 are X, Z and Y, respectively, and bonding of monomeric units occurs at C-4, C-6 or C-8;
  when any C-4, C-6 or C-8 is not bonded to another monomeric unit, X, Y and Z independently are hydrogen or a sugar; and
  the sugar is optionally substituted with a phenolic moiety at any position, for instance, via an ester bond.

For example, the above method may involve use of a compound An, or a pharmaceutically acceptable salt or derivative thereof (including oxidation products, methylated derivatives and glucuronidated derivatives), wherein R is OH, and when any C-4, C-6 or C-8 is not bonded to another monomeric unit, X, Y and Z are hydrogen. Examples of suitable sugars are as described above. Examples of phenolic moieties are as described above. Examples of derivatives are as described above.

In certain embodiments, the invention provides (i) a method of enhancing an executive cognitive function and/or (ii) a method of increasing blood flow in brain vasculature, each comprising administering to a mammal (e.g. human) or a veterinary animal in need thereof, a composition comprising an effective amount of a compound having the formula An, or a pharmaceutically acceptable salt or derivative thereof (including oxidation products, methylated derivatives, and glucuronidated derivatives):

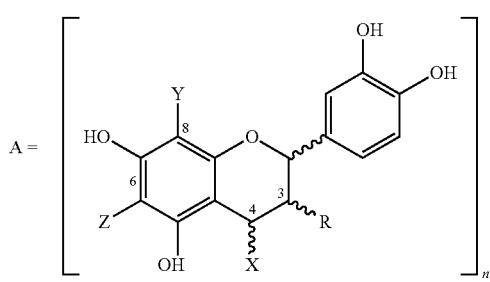

wherein
- n is an integer from 2 to 18;
- R and X each have either α or ρ stereochemistry;
- R is OH;
- the substituents of C-4, C-6 and C-8 are X, Z and Y, respectively, and bonding of monomeric units occurs at C-4, C-6 and C-8; and
- when any C-4, C-6 or C-8 is not bonded to another monomeric unit, X, Y and Z are hydrogen.

Examples of the compounds useful for the products and in the methods of the invention include the compounds described herein wherein the integer n is 3 to 18; 2 to 12; 3 to 12; 2 to 5; 4 to 12; 5 to 12; 4 to 10; or 5 to 10. In some embodiments, the integer n is 2 to 4, for example 2 or 3. This disclosure applies to any compound of formula An herein.

While any human or a veterinary animal can benefit from the methods described herein, it will be understood that a "subject in need thereof" is a subject in imminent need of enhancement of cognitive function or a subject having a profession (or performing tasks) that require(s) constant utilization of executive cognitive function(s). Examples of subjects in need of enhancement of cognitive function(s) and/or increased brain blood flow will be apparent to those of skill in the art, for example subjects who will imminently participate in a competitive event (e.g. those appearing in an examination, competing in sporting/athletic events, attending a job interview); those addressing an audience/gathering (e.g. educators, politicians, live television-news anchors, reporters); entertainers (e.g. movie actors and live-show performers); and those engaged in tasks involving intense periods of mental processing. Also included are subjects who perform tasks requiring complex decision making and multitasking, for example high-profile business executives; transportation workers (e.g. bus drivers, railway engine drivers, airline pilots, ship captains/commanders); construction workers (e.g. high-risk constructions such as bridges, high-rise buildings, roadways and railways on mountains); defense personnel (e.g. warship commanders, warrior aircraft pilots, pilots of naval vessels). Further, an elderly/aged individual (for example >65, e.g. >75) who is experiencing cognitive decline but has not been clinically diagnosed with a neurodegenerative disease will also benefit from the compositions and methods described herein.

The present compounds may be administered orally in the form of a cocoa component, for example cocoa nibs or fragments thereof, chocolate liquor, cocoa sol ds (e.g. partially and fully-defatted cocoa solid, e.g. of cocoa solids is cocoa poWder), cocoa extract or fraction thereof, or may be added independently of cocoa components. The cocoa component may be prepared such that the content of cocoa polyphenols (CP) is preserved for example by altering traditional processing steps, as described, for example, in U.S. Pat. Nos. 6,194,020 and 6,599,553.

In some embodiments, the present compounds may be administered in combination with other cognition-enhancing agents and/or to enhance responsiveness to other cognition-enhancing agents. Examples of cognition-enhancing agents include: metabolic substrates (e.g., glucose, ketones, supplemental oxygen), alkaloids (e.g., theobromine, caffeine) vitamins, amino acids, minerals, micronutrients, botanical extracts or their derivatives, herbs or herbal supplements (e.g., ginkgo, ginseng).

Thus, the following uses are within the scope of the invention. Use of a flavanol, or a pharmaceutically acceptable salt or derivative thereof (including oxidation products, methylated derivatives, and glucuronidated derivatives) as defined above, in the manufacture of a medicament, food, nutraceutical or dietary supplement for enhancing an executive cognitive function and/or for increasing blood flow in brain vasculature. Use of a compound of formula An, or a pharmaceutically acceptable salt or derivative thereof (including oxidation products, methylated derivatives and glucuronidated derivatives), as defined herein, in the manufacture of a medicament, food, nutraceutical or dietary supplement for use in enhancing an executive cognitive function and/or for increasing blood flow in brain vasculature.

The effective amount may be determined by a person of skill in the art using the guidance provided herein and general knowledge in the art. For example, the effective amount may be such as to achieve a physiologically relevant concentration in the body of a mammal. Such a physiologically relevant concentration may be at least 20 nanomolar (nM), preferably at least about 100 nM, and more preferably at least about 500 nM. In one embodiment, at least about one micromole in the blood of the mammal, such as a human, is achieved. The compounds defined herein, may be administered at from about 35 mg/day, 40 mg/day or 50 mg/day (e.g. to about 1000 mg/day), or from about 75 mg/day (e.g. to about 1000 mg/day), or from about 100-150 mg/day (e.g. to about 900 mg/day), or from about 300 mg/day (e.g. to about 500 mg/day). However, amounts higher than exemplified above may be used since the upper end of the amount range is not a limiting factor. The amounts may be measured as described in Adamson, G. E. et al., *J. Ag. Food Chern.;* 1999; 47 (10) 4184-4188.

The administration may be continued as a regimen, i.e., for an effective period of time, e.g., daily, monthly, bimonthly, biannually, annually, or in some other regimen, as determined by the skilled medical practitioner for such time as is necessary. The administration may be continued for at least a period of time required for enhancement of executive cognitive function(s) and/or for increasing blood flow in brain vasculature. The composition may be administered daily, preferably two or three times a day, for example, morning and evening to maintain the levels of the effective compounds in the body of the mammal. To obtain the most beneficial results, the composition may be administered for at least 7 days, or at least 14 days, or at least 30 days, or at least 45 days, or at least 60 days, or at least 90 days. These regimens may be repeated periodically as needed.

Compositions and Formulations

The compounds of the invention may be administered as a food (including pet food), a food additive, or a dietary supplement, or a pharmaceutical.

As used herein, "food" is a material containing protein, carbohydrate and/or fat, which is used in the body of an organism to sustain growth, repair and vital processes and to furnish energy. Foods may also contain supplementary substances, for example, minerals, vitamins and condiments. See Merriam-Webster's Collegiate Dictionary, 10th Edition, 1993. The term food includes a beverage adapted for human or animal consumption. As used herein a "food additive" is as defined by the FDA in 21 C.F.R. 170.3(e)(1) and includes direct and indirect additives. As used herein, a "dietary supplement" is a product (other than tobacco) that is intended to supplement the diet that bears or contains one or more of the following dietary ingredients: a vitamin, a mineral, an herb or other botanical, an amino acid, a dietary substance for use by man to supplement the diet by increasing the total daily intake, or a concentrate, metabolite, constituent, extract or combination of these ingredients. As used herein, a "pharmaceutical" is a medicinal drug. See Merriam-Webster's Collegiate Dictionary, 10th Edition, 1993. A pharmaceutical may also be referred to as a medicament. The above compositions may be prepared as is known in the art.

The compositions may contain a carrier, a diluent, or an excipient. Depending on the intended use, the carrier, diluent, or excipient may be chosen to be suitable for human or veterinary use, food, additive, dietary supplement or pharmaceutical use. The composition may optionally contain an additional cognition-enhancing/improving agent. Also depending on use, a person of skill in the art may select the degree of purity of the compound of the invention. For example, when used to prepare pharmaceutical dosage forms, the compound should be as pure as commercially possible, while when preparing food, additive, or supplement, less pure or mixtures of compounds (e.g. plant extracts) may be used.

The compound of the invention may be "isolated and purified," i.e., it may be separated from compounds with which it naturally occurs (e.g. when the compound is of natural origin), or it may be synthetically prepared, in either case such that the level of contaminating compounds and/or impurities does not significantly contribute to, or detract from, the effectiveness of the compound. For example, an "isolated and purified B2 dimer" is separated from B5 dimer, with which it may occur in nature (e.g. in cocoa bean), to the extent achievable by the available commercially viable purification and separation techniques. Such compounds are particularly suitable for pharmaceutical applications.

The compound may also be less pure, i.e., "substantially pure," i.e., it may possess the highest degree of homogeneity achievable by available purification, separation and/or synthesis technology but need not be separated from the like compounds. As used herein, "the like compounds" are the compounds having the same degree of polymerization. For example, a "substantially pure dimer" refers to a mixture of dimers (e.g. B2 and B5, as it would occur in a cocoa extract fraction). While less suitable for pharmaceutical applications, such "substantially pure" compounds may be utilized for food, food additive and dietary supplement applications.

In some embodiments, the compound of the invention is at least 80% pure, at least 85% pure, at least 90% pure, at least 95% pure, at least 98% pure, or at least 99% pure. Such compounds are particularly suitable for pharmaceutical applications.

Pharmaceuticals containing the inventive compounds, optionally in combination with another cognition-enhancing/improving agent may be administered orally. As used herein, "oral administration" includes administration by the mouth and includes sublingual and buccal administrations. A person of skill in the art will be able to determine a suitable mode of administration to maximize the delivery of the compounds of the invention. Thus, dosage forms adapted for each type of administration by mouth are within the scope of the invention and include solid, liquid and semi-solid dosage forms, such as tablets, capsules, gelatin capsules (gelcaps), bulk or unit dose powders or granules, emulsions, suspensions, pastes, or jellies. Sustained-release dosage forms are also within the scope of the invention. Suitable pharmaceutically acceptable carriers, diluents, or excipients are generally known in the art and can be determined readily by a person skilled in the art. The tablet, for example, may comprise an effective amount of the compound of the invention and optionally a carrier, such as sorbitol, lactose, cellulose, or dicalcium phosphate.

The foods comprising the compounds described herein and optionally another cognition-enhancing/improving agent may be adapted for human or veterinary use, and include pet foods. The food may be other than a confectionery, for example, a beverage (e.g. cocoa flavored beverage). A confectionery such as a standard of identity (SOI) and non-SOI chocolate, such as milk, sweet and semi-sweet chocolate including dark chocolate, low fat chocolate and a candy which may be a chocolate covered candy are also within the scope of the invention. Other examples include a baked product (e.g. brownie, baked snack, cookie, biscuit) a condiment, a granola bar, a toffee chew, a meal replacement bar, a spread, a syrup, a powder beverage mix, a cocoa or a chocolate flavored beverage, a pudding, a rice cake, a rice mix, a savory sauce and the like. If desired, the foods may be chocolate or cocoa flavored. Food products may be chocolates and candy bars, such as granola bars, containing nuts, for example, peanuts, walnuts, almonds, and hazelnuts. The food is designed to deliver an effective amount of the compounds described herein.

The compounds for use in the present invention may be of natural origin, for example, derived from a cocoa bean or another natural source known to a person of skill in the art, or prepared synthetically. A person of skill in the art may select natural or synthetic polyphenols based on the use and/or availability or cost.

The compounds may be included in the composition in the form of a cocoa component. For example, the compound(s) may be included in the composition in the form of a cocoa ingredient, for example, chocolate liquor included in chocolate, or may be added independently of cocoa ingredients, for example, as an extract, extract fraction, isolated and purified individual compound, pooled extract fractions or a synthetically prepared compound. The extraction and purification may be conducted as described in U.S. Pat Nos. 5,554,645 and 6,670,390 to Romanczyk et al., and U.S. Pat. No. 6,627,232 to Hammerstone et al., each of which is hereby incorporated herein by reference.

Cocoa flavanols and/or procyanidins may be provided in the composition of the invention by cocoa ingredients containing these compounds or by including chocolate, which may be milk, sweet and semi-sweet, and is preferably dark chocolate, and low fat chocolate. The cocoa ingredients may be prepared using traditional cocoa processing procedures but is preferably prepared using the method described in U.S. Pat. No. 6,015,913 to Kealey et al. Alternatively, to enhance the level of cocoa polyphenols, chocolate liquor and cocoa solids prepared from cocoa beans having a fermentation factor of 275 or less may be used. These ingredients have cocoa polyphenol content that is higher than can be obtained using traditional cocoa processing methods (e.g. with roasting and fully fermented beans). The chocolate may be prepared using conventional techniques from the ingredients described above or using an improved process for preserving cocoa polyphenols during chocolate manufacturing as described in the International Appl. No. PCT/US99/05414 published as WO99/45788 and in its U.S. counterpart, U.S. Pat. No. 6,194,020, the relevant portions of which are hereby incorporated herein by reference. A chocolate prepared by at least one of the following non-traditional processes is referred to herein as a "chocolate having a conserved amount of cocoa polyphenols": (i) preparing cocoa ingredients from underfermented or unfermented cocoa beans; (ii) preserving cocoa polyphenol during cocoa ingredient manufacturing process; and (iii) preserving cocoa polyphenol during chocolate manufacturing process. Such non-traditional processes may be used to prepare other cocoa component-containing products (foods e.g. beverages, dietary supplements) designed to contain enhanced levels of flavanols and/or procyanidins.

Synthetic procyanidins may also be used and are prepared by methods known in the art and as described, for example, as in U.S. Pat. Nos. 6,420,572; 6,156,912; and 6,864,377, the relevant portions of each of which are hereby incorporated herein by reference.

A daily effective amount of the compound of the invention may be provided in a single serving in case of a food or a single dosage in case of a pharmaceutical or a dietary supplement. For example, a confectionery (e.g. chocolate) may contain at least about 100 mg/serving (e.g. 150-200, 200-400 mg/serving).

The dietary supplement containing the compounds of the invention, and optionally another cognition-enhancing/improving agent, may be prepared using methods known in the art and may comprise, for example, nutrient such as dicalcium phosphate, magnesium stearate, calcium nitrate, vitamins, and minerals.

Further within the scope of the invention is an article of manufacture such as a packaged product comprising the composition of the invention (e.g. a food, a dietary supplement, a pharmaceutical) and a label indicating the presence of, or an enhanced content of the inventive compounds, or directing use of the composition to enhance executive cognitive function(s) and/or to increase blood flow in brain vasculature. The packaged product may contain the composition and the instructions for use to enhance executive cognitive functions and/or to increase blood flow in brain vasculature. The label and/or instructions for use may refer to any of the methods of use described in this application.

The invention also relates to a method of manufacturing an article of manufacture comprising any of the compositions described herein, packaging the composition to obtain an article of manufacture and instructing, directing or promoting the use of the composition/article of manufacture for any of the uses described herein. Such instructing, directing or promoting includes advertising.

The invention is further described in the following non-limiting examples.

EXAMPLES

Example 1: Effect of Cocoa Flavanols on the fMRI Response to a Cognitive Task in Healthy Young People Methods
Subjects Sixteen young female subjects between the ages of 18 and 30 yr participated in the study under the following exclusion criteria: no history of migraines, stroke, hypertension, diabetes, or any neurological or vascular disease and no use of tobacco products. All subjects had normal vision and normal color vision, were not dyslexic, were right handed and their first language used the 'Roman' alphabet. Subjects average daily caffeine intake was estimated from their responses to a dietary questionnaire and they were all classified as low caffeine users (<120 mg/day). All subjects were instructed to refrain from alcohol and caffeine, or from using any medication for 12 hrs before each visit for the fMRI measurements. The local Medical School Research Ethics Committee approved this study and all subjects gave informed written consent before taking part in the study.

Each subject underwent two fMRI sessions that were repeated at least 14 days apart. Subjects were randomized to receive a high flavanol cocoa drink (150 mg flavanollprocyanidins per drink for 5 days prior to one fMRI session and a low flavanol cocoa drink (13 mg flavanol/procyanidin per drink) for 5 days prior to the other session in a double blind counterbalanced manner. These will be referred to hereafter as 'high flavanol' and 'low flavanol'. Subjects consumed one drink per day at a set time for the 5 days prior to each scan session, with the final drink being consumed approximately 1.5 hours before the fMRI scan.

Study Design

Subjects were pre-trained to perform two tasks, a number task of odd-even judgment and a letter task requiring consonant-vowel judgment. In the letter task subjects learnt to respond to single letter stimuli depending on whether the letter displayed was a consonant (G, K, M, R) or a vowel (A, E, O, U). Subjects were trained to press a left button in response to a vowel and right button for a consonant. In the number task, subjects were trained to respond to digits that were either odd (3, 5, 7, 9) or even (2, 4, 6, 8), using left and right button responses respectively.

Once subjects were familiarized with the rules of the letter and number tasks, they were trained on the letter-digit pairs task to be performed in the fMRI study. The letter-digit pairs task consisted of a letter and a digit displayed simultaneously on a computer screen (for the fMRI scanning a projector and screen were used). The letter-digit pairs were either red or blue. When letter-digit pairs were presented in red, subjects were instructed to attend to the letter and respond by pressing the appropriate button as trained (i.e., applying the rule for categorizing as vowel or consonant). If the letter-digit pair was blue they responded to the digit (odd-even judgment) in a similar manner.

In this study the definition of the 'switch' task is the changing between the two sets of rules, one for the letters (consonant-vowel judgment) and one for digits (odd-even judgment). To create a paradigm comprising of 'switch' and 'non-switch' conditions, the letter-digit pairs were grouped into blocks. A block of five letter-digit pairs, all of the same color is a 'non-switch' block. A block of five letter-digit pairs alternating between red and blue stimuli (and so reconfiguring task judgment) is a 'switch' block. The gap between each letter-digit pair within the block was 3 seconds, giving a total block length of 15 seconds; this was then followed by a 12 second fixation cross (baseline condition). The blocks were presented alternately (i.e., 'switch' block, 'non-switch' block, 'switch' block, 'non-switch' block etc.). The presentation of letter-digit pairs within a block helps to increase the switch cost and so also increase the magnitude of the fMRI BOLD response, whilst the 12 second interval between the blocks allows the BOLD response to return to baseline.

Prior to the fMRI study the subjects were trained to a competent level (error rates below 5%) in the task by performing five blocks of 'switch' and 'non-switch' trials. During the fMRI study twenty blocks of 'switch' trials and 20 blocks of 'non-switch' trials were performed in the study, resulting in a total study duration of 18 minutes.

fMRI Scanning

A 3.0 T purpose-built scanner was used with TEM head coil and insert head gradient coil. T2*-weighted coronal echo-planar images (EPI) with a 128×64 matrix size, 3 mm in-plane resolution and 9 mm slice thickness were acquired using MBEST acquisition sequence with 30 ms echo time (TE) and 1.9 kHz gradient switching frequency. Sixteen contiguous coronal slices were acquired every 3 seconds (TR=3 s). Throughout the study subjects reaction time and error rate data was recorded. Further the subjects' heart rate was monitored. Following the fMRI study a 64 slice EPI set was acquired to aid anatomical localization.

fMRI Data Processing

The fMRI data was processed using SPM99 (Friston K J et al., *Neuroimage* 1995; 2:166-172) (Statistical Parametric Mapping, Wellcome Department of Imaging Neuroscience, UK). The raw data from the scanner was motion corrected to realign all functional slices to the first volume of the data set, spatially normalized to the standard EPI template. Eight millimeter FWHM (full width half maximum) spatial smoothing and 128 s high pass filter cut-off were applied.

A general linear model design matrix was created within SPM99 that modelled the paradigm. 'Switch' and 'non-switch' blocks were modelled as 12 s box functions. The paradigm time course was then convolved with the canonical haemodynamic response function and its temporal derivative. Statistical parametric maps (SPM's) of the 'switch' condition and 'non-switch' condition vs baseline were formed. In addition, direct comparison between the two activation conditions (i.e., 'switch' vs. baseline and 'non-switch' vs. baseline) was also performed at a corrected significance level of P<0.05, with the respective activation vs. baseline comparisons ('switch' vs baseline and 'non-switch' vs baseline) being used as a mask.

Cerebral Blood Flow (CBF) Measurements and Analysis

In this initial study on four subjects (24 to 31 yr) we assessed the time course of the effect of flavanols on brain blood flow. A cerebral blood flow (CBF) map was acquired using an EPISTAR (Echo-Planar MR Imaging and Signal Targeting with Alternating Radiofrequency) arterial spin labelling sequence (ASL) on five multi-slice axial 7 mm slices. Diffusion weighting (b=5 mm$^2$/s) was applied for suppression of intra-arterial spins. A hyperbolic secant pulse was used for the labelling, and the tag and control slabs were 9 cm in width with an inversion time (TI) of 1400 ms. The EPISTAR sequence was implemented with repetition time (TR) of 3 seconds between tag and control images, and a total of 60 tag and control pairs were acquired. Each subject underwent CBF imaging prior to and at 2, 4, and 6 hours after ingestion of a high flavanol cocoa drink (450 mg flavanol) or a low flavanol cocoa drink, on two separate occasions. In this study, in contrast to the fMRI study, a single dose of the drinks was consumed on only one occasion. Each CBF measurement was followed by the acquisition of a $T_1$ map for segmentation of brain tissue types and grey matter territories. (CBV is commonly used to refer to blood volume).

Cerebral blood flow data were first segmented into grey and white matter regions using masks generated from the $T_1$ map. Grey matter CBF maps were then further segmented into territories fed by major vessels (Yen Y-F et al., *Magn Reson Med* 2001: 47:921-928; hereby incorporated herein by reference). Mean cerebral blood flow values were then calculated for white and grey matter regions. Whole grey matter perfusion values are presented here.

Results

Behavioural Results for Task Switching Paradigm

Figure 1:
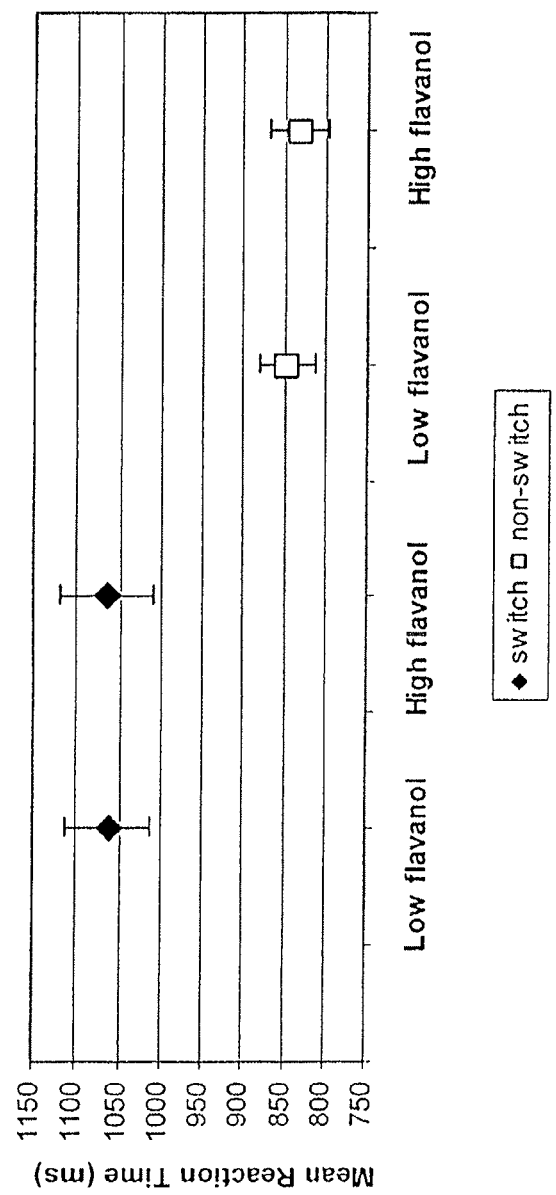
FIG. 1: shows mean reaction time (±SEM) for the letter-digit task. Reaction times were averaged over all subjects.

Robust switch costs in response times were observed. Each of the subjects was numerically slower for the 'switch' condition than 'non-switch' condition, both for the letter and number tasks, the constant switching from one task rule to the other proving difficult. The mean reaction times across the group for the 'switch' and 'non-switch' blocks are shown in FIG. 1. The significance of the switch cost was p=5×10$^{-6}$ for 'low flavanol' and p=1×10$^{-6}$ for 'high flavanol'. There was no significant difference in the switch cost between the two drinks (p=0.30). The average switch cost was 224±25 milliseconds (ms).

The possibility that during the 40 blocks of 'switch' and 'non-switch' trials of the fMRI study the subjects would either make more or less errors as they either became fatigued or improved due to learning effects was also investigated. Analysis of the reaction time responses revealed that no significant fatigue/learning effects occurred over the course of the fMRI sessions (p=0.74). Also the drink order was randomized and a comparison of the reaction time responses between first and second scanning sessions made, this again revealed no significant differences (p=0.73).

Heart Rate Results for Task Switching Paradigm

The mean heart rate for the 'switch' and 'non-switch' conditions for the low and high flavanol cocoa drinks was measured as shown in Table 1. Paired t-tests were performed to determine any differences in heart rate between the 'switch' and 'non-switch' conditions; for both drinks there was a significant increase in heart rate for the 'switch' condition compared to 'non-switch' condition ('low flavanol': 'switch'>'non-switch' p=0.01; 'high flavanol': switch'>'non-switch' p=0.0009). No significant difference in heart rate was found between the low and high flavanol drinks.

TABLE 1

The mean heart rate(±SEM) (beats per minute) in response to 'switch' and 'non-switch' conditions for low and high flavanol drinks.

|  | Low flavanol | High flavanol |
| --- | --- | --- |
| Switch | 66.8 +/− 2.6 | 67.6 +/− 2.6 |
| Non-switch | 63.0 +/− 2.5 | 64.2 +/− 3.0 | fMRI Results for Task Switching Paradigm

Figure 2A:
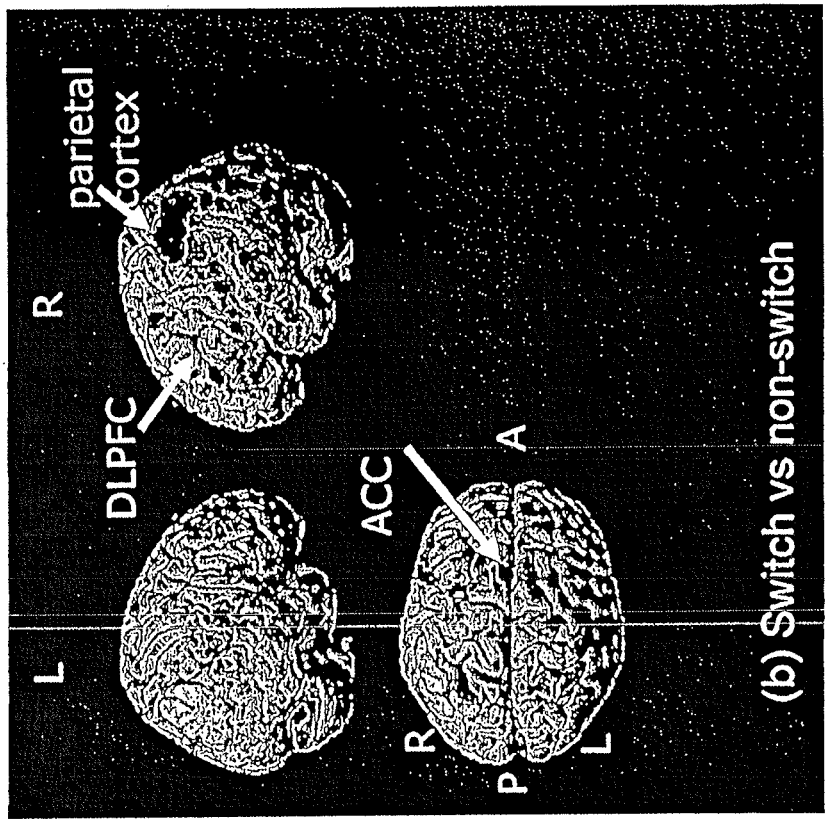
FIG. 2A: shows task-related activity in the 'switch' versus baseline condition for 'high flavanol'. Statistical parametric maps thresholded at $P<0.05$ (corrected) for height and spatial extent.

FIG. 2a shows the group statistical parametric map for the switch task vs baseline condition at a corrected probability of P<0.05. The 'switch' and 'non-switch' versus baseline conditions revealed activation in the medial and lateral prefrontal cortex (including the dorsolateral prefrontal cortex (DLPFC)), parietal cortex, anterior cingulate cortex (ACC), and cerebellum. 'Non-switch' is not represented in FIG. 2a, however, 'non-switch' vs baseline condition shows similar areas to the 'switch' vs baseline condition.

The brain areas outlined above have previously been shown to be associated with task switching (Lewis P A et al., *Curr Opin Neurobiol* 2003; 13:250-255; Sohn M H et al., *Proc Natl Acad Sci USA* 2000; 97:13448-53; Swainson R et al., *J Cogn Neurosci* 2003; 15:785-99). Further, a number of cognitive neuroimaging studies aside from task-switching have found similar patterns of activation. These include working memory (Cabeza et al., *Neuroimage* 2002: 16:317-330; Postle B et al., *Proc Natl Acad Sci USA* 1999; 96:12959-12964), memory retrieval (Thompson-Schill S L et al., *Proc Natl Acad Sci USA* 1997: 94:14792-14797; Wagner A D et al., *Neuroimage* 2000; 14:1337-1347), and arithmetic problem solving tasks (Anderson J R et al., *Psychonom Bull Rev* 2003; 10:241-261; Dehaenae S et al., *Science* 1999; 284:970-974). All such tasks demonstrate strong prefrontal-parietal interconnections (Petrides *Metal., J Comp Neuro*/1984; 228:105-116; Schwartz M L et al., *J Comp Neuro*/1984; 226:403-420), suggesting that these two areas may serve complementary roles in the high-level cognition.

Figure 2B:
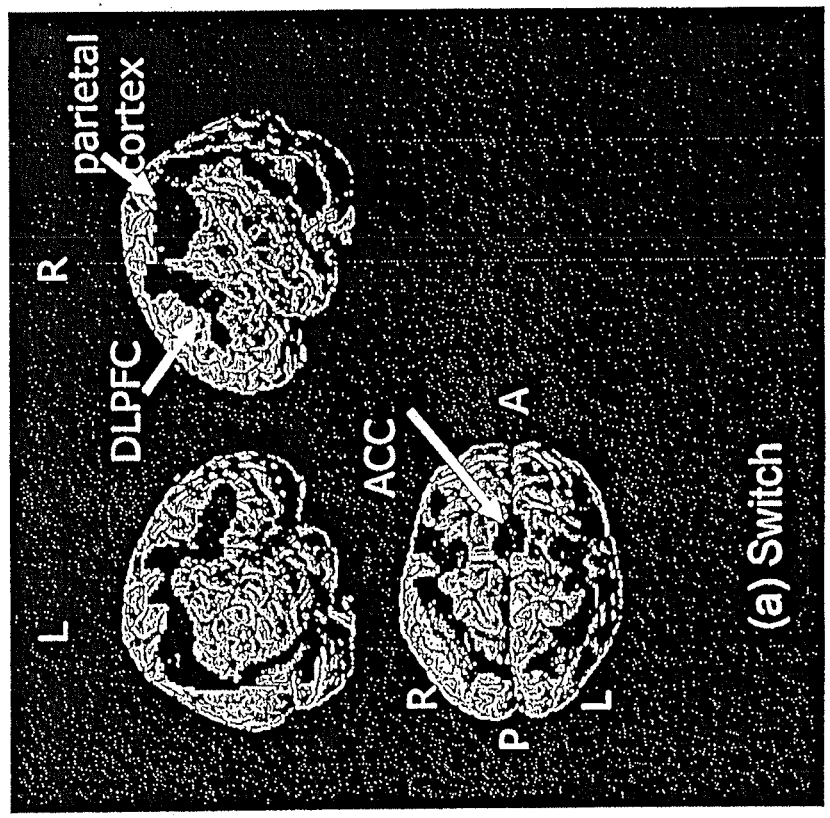
FIG. 2B: shows task-related activity for the comparison between 'switch' and 'non-switch' conditions ('switch' versus baseline>'non-switch' versus baseline) for 'high flavanol'. Statistical parametric maps thresholded at $P<0.05$ (corrected) for height and spatial extent.

FIG. 2b shows the group statistical map of areas of activation which show significantly increased BOLD response during the 'switch' task relative to the 'non-switch' task. From this comparison, it can be seen that those brain areas activated preferentially to the 'switch' condition are largely localized in the right hemisphere, in the dorsolateral prefrontal and parietal cortices, as well as the anterior cingulate cortex and cerebellum.

FIG. 2a shows areas for the 'switch' condition relative to a resting baseline. These are all those parts of the brain which are associated with performing the switch task, so are not exclusive to task switching since they can include areas associated with different aspects of the task such as the motor response to the button press.

Referring to FIGS. 2a-b, FIG. 2b shows areas which are greater for the 'switch' condition than the 'non-switch' condition. Therefore, this can be thought of as ('switch' condition relative to a resting baseline)–('non-switch' condition relative to a resting baseline). This is the important condition as the aspects of the task which are unimportant, such as the motor response to the button press, are in both the 'switch' and 'non-switch' conditions and so by subtracting 'non-switch' from 'switch' those brain areas associated with the motor button press response are removed. In the 'switch' minus 'non-switch' condition only those areas which are purely involved in task switching are seen.

In task-switching it is thought that the anterior cingulate cortex (ACC) detects conflict in a task-setting (Gehring W J and Knight R T, *Nat Neurosci* 2000; 3:516-20), the right frontal cortex plays a role related to the inhibition of irrelevant (preceding) responses (Aron et al., *Trends Cogn Sci* 2004:8:170-7), and the active maintenance of information that is newly loaded into working memory (Goldman-Rakic P S, *Annu Rev Neurosci* 1988; 11:137-156). The right posterior parietal cortex has widely been shown to be responsible for spatial or visual attention (Rushworth M F S et al., *J Neurosci* 2001; 21: 5262-5271), whilst the cerebellum is thought to be primarily activated with timing irregularity in the switch task, consistent with its role as an internal timing system (Ivry R B, *Curr Opin Neurobio*/1996; 6:851-7).

Statistical comparison of the BOLD signal change between the 'low flavanol' and 'high flavanol' conditions revealed that the 'high flavanol' generated a significantly greater BOLD signal change for both the activation ('switch' and 'non-switch') versus baseline conditions as well as for the comparison of 'switch' vs baseline with 'non-switch' vs baseline condition. Table 2 shows the average percentage signal change for the 'switch' BOLD response relative to baseline, for selected regions of interest, following ingestion of 'low' and 'high' flavanol drinks.

TABLE 2

The average percentage signal change(±SEM) of the BOLD response relative to baseline for the 'switch' condition following ingestion of a repeated dose of low and high flavanol drinks. The high flavanol drink revealed a marked increase in the BOLD response.

|  | Low flavanol | High flavanol |
| --- | --- | --- |
| Dorsolateral prefrontal cortex (DLPFC) | 2.3 ± 0.2 | 3.0 ± 0.2 |
| Parietal cortex | 2.1 ± 0.3 | 2.5 ± 0.2 |
| Anterior Cingulate Cortex (ACC) | 1.7 ± 0.1 | 2.1 ± 0.3 |

Cerebral Blood Flow (CBF) Time Course Results

Figure 3:
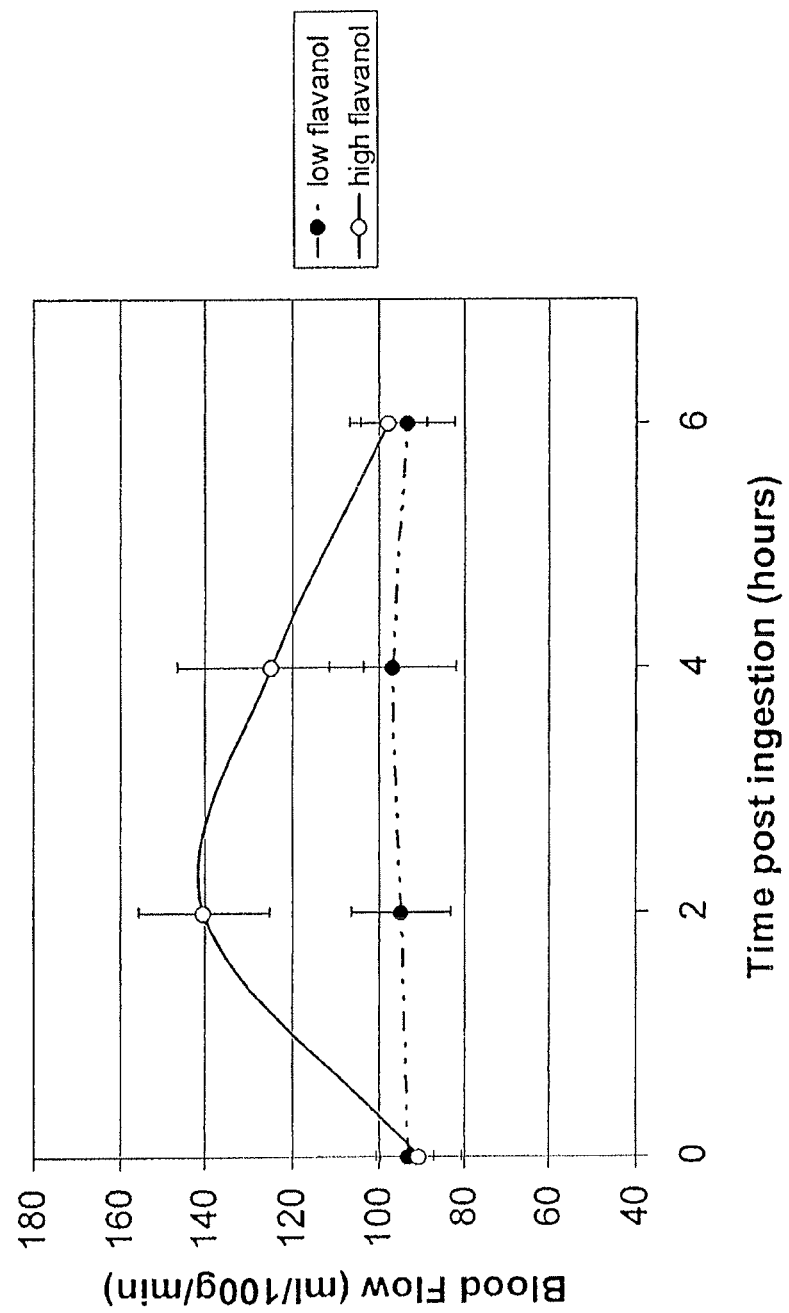
FIG. 3: shows the time course of the mean cerebral blood flow responses (±SEM) across grey matter (n=4) following ingestion of an acute dose of high flavanol drink and low flavanol drink.

FIG. 3 shows the time course of the mean cerebral blood flow response across grey matter following ingestion of the low and high flavanol drinks. It can be seen that there was an increase in cerebral blood flow in response to the high flavanol drink, with a peak in the cerebral blood flow response occurring at approximately two hours post ingestion, and CBF returning to baseline after approximately six hours. It should be noted that in this study an acute dose of flavanols was given, in contrast to the repeated dose given in the tMRI study.

ASL studies have previously been performed to measure the effects of hypercapnia, which induces cerebral vasodilation and CBF increases. Such studies have shown a CBF increase from 30% up to 87% in response to an expiration breath hold, which leads to an instantaneous increase in PaCO$_2$ (Li T Q et al., *Neuroimage* 1999; 10:562-9; Li T Q et al., *Neuroimage* 1999; 9:243-9; Kastrup A et al., *AJNR Am J Neuroradio*/1999; 20:1233-8). Direct effects of inhalation of 5% $CO_2$ as a vasodilative stimulus have revealed global CBF increases of approximately 87% (Kastrup A et al., *Magn Reson Imaging* 2001; 19:13-20). The 60% CBF changes shown here at two hours post ingestion of the high flavanol drink are of a similar order to these effects.

Example 2: Evaluation of the Behavioral Effects of Cocoa Polyphenols

Methods

Study Design

The study followed a double-blind, placebo-controlled, balanced crossover design and examined the cognitive effects of multi-dose of polyphenols in a cocoa drink. Participants (N=30; 13 male and 17 female, mean age 21.93 years, SEM 0.61, range 18-35 years) were healthy young adults who were screened for appropriate, potentially compromising relevant health conditions and dietary factors. The participants in the study visited the laboratory on five occasions. The first visit comprised of a practice day where subjects were familiarized with the procedure, this visit also served to ensure that all performance scores were within norms for the batteries. Subsequent visits made up the four study days that were conducted not less than 3 days apart to ensure a sufficient wash out between conditions, where the subjects were randomly allocated to a Latin Square cell dictating treatment order.

Participants abstained from caffeine and alcohol for a minimum of 12 hours prior to the first testing session and throughout the morning until the final testing session was completed. A diary was provided to allow participants to record all food and drink consumption for 24 hours prior to the first test session of each study day. It was recommended to participants that they avoid food and beverages which are high in flavonoid content for 24 hours preceding each study day.

Treatments

Participants received three drinks containing: 1) 36.4 mg cocoa polyphenols (control), 2) 469.3 mg cocoa polyphenols (medium CP), 3) 902.2 mg polyphenols (high CP) on separate occasions. In each case the treatment was made up of two sachets of powder mixed with 200 ml hot water. As well as 33% cocoa powder the drinks also contained the following: non-fat dry milk powder (59.0%); fiber (5.6%); emulsifier (0.8%); cellulose gel (0.55%); xanthan gum (0.55%); artificial and natural vanilla (0.1%); and sucralose (0.1%). Five minutes was allowed for drink consumption.

The composition of each treatment or control sachet was as follows:

TABLE 3

| CP composition | | |
|---|---|---|
| | HIGH CP % | Control % |
| Monomers | 24.8 | 27 |
| Epicatechin | 18.6 | 10.1 |
| catechin | 6.2 | 16.9 |
| dimers | 18.3 | 22.2 |
| trimers | 14.2 | 7.9 |
| tetramers | 12.7 | 5.3 |
| pentamers | 9.8 | 3.9 |
| hexamers | 8.3 | 5.7 |
| heptamers | 3.8 | 4.7 |
| odamers | 3 | 5 |
| nonamers | 4.3 | 11.9 |
| decamers | 0.8 | 6.4 |
| total | 100 | 100 |

TABLE 4

| | High CP product | Control product |
|---|---|---|
| Packet code | 852 | 217 |
| Packet size, g | 31 | 31 |
| Mg CP | 451.1 | 18.2 |
| Calories | 118.7 | 117.2 |
| Total fat, g | 1.4 | 1.5 |
| Sat. fat, g | 0.8 | 0.8 |
| Cholesterol, mg | 4.4 | 4.9 |
| Sodium, mg | 105.1 | 155.0 |
| Total Carbo., g | 17.1 | 16.5 |
| Dietary Fiber, g | 3.0 | 3.9 |
| Sugars, g | 9.4 | 9.2 |
| Protein, g | 9.4 | 9.4 |
| mg caffeine | 18.3 | 21.2 |
| mg theobromine | 336.5 | 327.4 |

TABLE 55

| Minerals | | |
|---|---|---|
| | High CP product mg/lg | Control product mg/g |
| Sodium, mg | 105.1 | 155.0 |
| Potassium, mg | 530.1 | 644.8 |
| Calcium, mg | 243.7 | 241.2 |
| Iron, mg | 1.9 | 2.9 |
| Phosphorous, mg | 280.2 | 265.4 |
| Magnesium, mg | 85.9 | 78.4 |
| Zinc, mg | 1.6 | 1.6 |

TABLE 55-continued

| Minerals | | |
|---|---|---|
| | High CP product mg/lg | Control product mg/g |
| Copper, mg | 0.4 | 0.4 |
| Manganese, mg | 0.6 | 0.6 |

To control micro/macro-nutrients and alkaloids, two packets were fed each time; for the high CP drink, two packets of high CP product were given; for the medium CP, one packet of high CP product and one packet of the control product were given; and for the control CP, two packets of the control product were given.

Assessment

Cognitive Demand Battery

In this study we undertook our 'Cognitive Demand Battery', (CDB). Participants received three drinks containing (i) 36.4 mg cocoa polyphenols (control), (ii) 469.3 mg cocoa polyphenols (medium CP), and (iii) 902.2 mg cocoa polyphenols (high CP). Study days involved the CDB consisting of Serial Threes (2 min), Serial Sevens (2 min), the Rapid Visual Information Processing task (RVIP, 5 min) and a mental demand visual analogue scale (1 min). On presenting to the laboratory a saliva sample was taken for analysis of caffeine levels. On each study day participants went through each of the tasks once to alleviate practice effects.

This was followed by a baseline session, immediately followed by the day's treatment for which up to 5 min was allowed. The end of drink consumption represented T=O. A period of 90 min was allowed for absorption, following which the participants underwent the CDB six times in immediate succession, followed by a second salivary sample for determination of caffeine levels. The objective of these tasks (in the CDB) was to assess the impact of treatment on continuous cognitive demand. The overall cognitive load in the session increases as participants complete three such tests repeatedly for a period of approximately one hour.

Serial Subtractions

These tasks assess the interaction between a given intervention and 'mental demand'.

A modified computerized version of the Serial Sevens test was utilized (Haskell, C. F. et al., *Psychopharmacology*, 2005, 179:813-825). The original verbal Serial Sevens test has appeared in a number of forms, including as part of the Mini-Mental State Examination for dementia. It has been used to assess cognitive impairment during hypoglycaemia, and has also been used to investigate the relationship between increased blood glucose levels and cognitive performance (Kennedy D. O. and Scholey, A. B., *Psychopharmacology*, 2000, 149:63-71; Scholey, A, B, et al., *Physiology & Behavior*, 2001, 73:585-592).

In the current studies computerized versions of Serial Subtractions were implemented, using tests of 2 minutes duration. For the Serial Sevens task a standard instruction screen informed the participant to count backwards in sevens from the given number, as quickly and accurately as possible, using the numeric keypad to enter each response. Participants were also instructed verbally that if they made a mistake they should carry on subtracting from the new incorrect number. A random starting number between 800 and 999 was presented on the computer screen, which was cleared by the entry of the first response. Each three-digit response was entered via the numeric keypad with each digit being represented on screen by an asterisk. Pressing the enter key signaled the end of each response and cleared the three asterisks from the screen. The task was scored for total number of subtractions and number of errors. In the case of incorrect responses, subsequent responses are scored as positive if they are correct in relation to the new number.

The Serial Threes task is identical to Serial Sevens, except that it involves serial subtraction of threes.

Rapid Visual Information Processing Task

This task has been widely used to study the cognitive effects of psychotropic interventions. The participants monitored a continuous series of digits for targets of three consecutive odd or three consecutive even digits. The digits were presented at the rate of 100 per minute and the participant responded to the detection of a target string by pressing a response key as quickly as possible. The task was continuous and lasted for 5 minutes, with 8 correct target strings being presented in each minute. The task was scored for percentage of target strings correctly detected, average reaction time for correct detections, and number of false alarms.

Subjective Scales {Mental Demand Visual Analogue Scale)

At the end of each set of tasks participants were asked to indicate how mentally fatigued they felt by marking a 100 mm line with the end-points labeled "not at all" and extremely.

Results

The results are shown in FIG. 4(a-d). Results show beneficial effects of a cocoa drink supplemented with flavanols/procyanidins on certain aspects of cognitive performance/abilities.

Example 3: Assessment of Acute Behavioral Effects of Cocoa Polyphenols on Mentally Non-Demanding Tasks Method This study allowed exploration of the effects of cocoa polyphenols independent of mentally-demanding situations and allowed to assess whether the effects of cocoa polyphenols were restricted solely to mentally-demanding situations.

Prior to participation in the study volunteers signed an informed consent form and completed a medical health questionnaire. All participants reported that they were in good health and free from social drugs and medication, with the exception of the contraceptive pill. Habitual smokers were excluded from the study.

Thirty participants were recruited into the study and informed that its aim was to investigate the cognitive and mood effects of a cocoa drink containing active components (one of which may be caffeine). Participants abstained from caffeine and alcohol for a minimum of 12 hours prior to the first testing session and throughout the morning until the final testing session was completed. A diary was provided to allow participants to record all food and drink consumption for 24 hours prior to the first test session of each study day and throughout the study visit. It was recommended to participants that they avoid food and beverages which are high in flavonoid content for 24 hours preceding each study day. This request for restricted flavonoid diet allowed acute changes in plasma flavanollevels to be monitored.

Salivary Caffeine Levels

Saliva samples were obtained using salivettes. Samples were taken immediately following baseline assessment in order to confirm compliance to overnight abstinence and immediately following each post-treatment assessment session to confirm uniform caffeine absorption across conditions. The saliva samples were immediately frozen at $-20°$ C. until thawing for in-house batch analysis using the Emit system (Syva, Palo Alto, USA). This is an enzyme immunoassay intended to measure caffeine as a metabolite and is based on competition for antibody binding sites between caffeine and an enzyme labelled drug.

Plasmajlavanollevels

Immediately prior to the baseline assessment and prior to the 90 minute post-treatment session a 2 ml venous blood sample was taken for determination of flavanollevels. These blood samples were collected by venipuncture using a monovette containing EDTA. The samples were then kept on ice until centrifuged at 3,000 rpm for 10 minutes at a temperature of $5°$ C. A Gilson pipette was used to measure 1485 Jll of the resulting plasma into an amber tube. A fresh solution of ascorbic acid (570 mM/100.4 mg/ml) was also prepared, kept on ice and away from light. 15 Jll of this solution was then added to the 1485 J.|| of plasma, mixed and stored at $-70°$ C. Unfortunately due to technical difficulties analyses of these samples was not possible.

Assessment

Cognitive Drug Research (CDR) Battery

The CDR system has been used in well over 500 European and North American drug trials, and has been shown to be sensitive to cognitive improvements as well as impairments with a wide variety of substances.

A tailored version of the battery was used, similar to that which has previously been found to be sensitive to improved cognitive function as a consequence of ingestion of numerous nutraceuticals. The selection of computer controlled tasks from the system was administered with parallel forms of the tests being presented at each testing session. Presentation was via color monitors on laptops, and, with the exception of written word recall tests, all responses were recorded via two-button (YES/NO) response boxes.

The entire selection of tests took approximately 20 minutes and were. administered in the following order:

Word Presentation: Fifteen words, matched for frequency and concreteness, were presented in sequence on the monitor for the participant to remember. Stimulus duration was 1 second, as was the inter-stimulus interval.

Immediate Word Recall: The participant was allowed 60 seconds to write down as many of the words as possible. The task was scored for number correct and errors.

Picture Presentation: Twenty photographic images for the participant to remember were presented sequentially on the monitor, at the rate of 1 every 3 seconds, with a stimulus duration of 1 second.

Simple Reaction Time: The participant was instructed to press the 'YES' response button as quickly as possible every time the word 'YES' was presented on the monitor. Fifty stimuli were presented with an inter-stimulus interval that varies randomly between 1 and 3.5 seconds. Reaction times were recorded in milliseconds.

Digit Vigilance Task: A target digit was randomly selected and constantly displayed to the right of the monitor screen. A series of digits was presented in the center of the screen at the rate of 80 per minute and the participant was required to press the 'YES' button as quickly as possible every time the digit in the series matches the target digit. The task lasted three minutes and there was 45 stimulus-target matches. Task measures were accuracy (%), reaction time (msec) and number of false alarms.

Choice Reaction Time: Either the word 'NO' or the word 'YES' was presented on the monitor and the participant was required to press the corresponding button as quickly as possible. There were 50 trials, of which the stimulus word was chosen randomly with equal probability, with a randomly varying inter-stimulus interval of between 1 and 3.5 seconds. Reaction times (msec) and accuracy (%) were recorded.

Spatial Working Memory: A pictorial representation of a house was presented on the screen with four of its nine windows lit. The participant was instructed to memorize the position of the illuminated windows. In 36 subsequent presentations of the house, one of the windows was illuminated and the participant decided whether or not this matched one of the lighted windows in the original presentation. The participant made their response by pressing the 'YES' or 'NO' response button as quickly as possible. Mean reaction times were measured in msec, and accuracy of responses to both original and novel (distractor) stimuli were recorded as percentages.

Numeric Working Memory: Five digits were presented sequentially for the participant to hold in memory. This was followed by a series of 30 probe digits for each of which the participant decided whether or not it had been in the original series and pressed the 'YES' or 'NO' response button as appropriate as quickly as possible. This was repeated two further times with different stimuli and probe digits. Mean reaction times were measured in msec, and accuracy of responses to both original and novel (distractor) stimuli were recorded as percentages.

Delayed Word Recall: The participant was again given 60 seconds to write down as many of the words as possible. The task was scored as number correct and errors.

Delayed Word Recognition: The original words plus 15 distractor words were presented one at a time in a randomized order. For each word the participant indicated whether or not she recognized it as being included in the original list of words by pressing the 'YES' or 'NO' button as appropriate and as quickly as possible. Mean reaction times were measured in msec, and accuracy of responses to both original and novel (distractor) stimuli were recorded as percentages.

Delayed Picture Recognition: The original pictures plus 20 distractor pictures were presented one at a time in a randomized order. For each picture participants indicated whether or not it was recognized as being from the original series by pressing the 'YES' or 'NO' button as appropriate and as quickly as possible. Mean reaction times were measured in msec, and accuracy of responses to both original and novel (distractor) stimuli were recorded as percentages.

The following tables indicate which stage of information processing each task assesses:

TABLE 6

Level 1: Attention
The ability to select, evaluate and respond
to appropriate environmental information

| | |
|---|---|
| Simple Reaction Time | Alertness |
| | Power of concentration |
| | Primary stage of information processing |
| Choice Reaction Time | As above, plus |
| | Stimulus discrimination |
| | Response organization |
| Task | Cognitive States and Processes Assessed |
| Digit Vigilance | Intensive vigilance |
| | Sustained concentration |
| | Ability to ignore distraction |

TABLE 7

Level II: Short Term or Working Memory
The ability to temporarily store the information relevant to ongoing tasks

| Task | Cog1litive States and Processes Assessed |
|---|---|
| Digit Scanning | Sub-vocal rehearsal of digit sequences |
| | Articulatory loop sub-system of working memory |
| Spatial Working Memory | Ability to temporarily retain spatial information |
| | Visuo-Spatial sub-loop of working memory |

TABLE 8

Level III: Long Term or Episodic Secondary Memory
The ability to register, store and retrieve
information over any period required

| Task | Cognitive States and Processes Assessed |
|---|---|
| Word Recall | Ability to store and recall verbal information |
| | Capacity for un-cued retrieval of words |
| | Episodic secondary verbal recall |
| Word Recognition | Ability (speed and sensitivity) to discriminate novel from previously presented words |
| | Episodic secondary verbal recognition |
| Picture Recognition | Ability to discriminate novel from previously presented pictorial information |
| | Episodic secondary non-verbal visual recognition |

Bond-Lader Visual Analogue Scales (Bond A., and Lader M., 1974, The use of analogue scales in rating subjective feelings, *British Journal of Psychology*, 47:211-218).

This measure was made up of 16 visual analogue scales with the end points anchored by antonyms: alert-drowsy, calm-excited, strong-feeble, muzzy-clearheaded, well coordinated-clumsy, lethargic-energetic, contented-discontented, troubled-tranquil, mentally slow-quick witted, tense relaxed, attentive-dreamy, incompetent-proficient, happy-sad, antagonistic-friendly, interested-bored, withdrawn-sociable. These were combined to form three "mood" factors: 'alert', 'calm' and 'content'.

Psychomotor Vigilance Task (Dinges D. F., and Powell J. W., 1985, Microcomputer analyses of performance on a portable, simple visual RT task during sustained operations. *Behavior Research, Methods, Instruments and Computers*, 17:652:655).

The psychomotor vigilance task (PVT) is a simple portable reaction time task used to evaluate sustained attention. The subject was instructed to press a button with the thumb of their dominant hand as soon as the stimulus appears (LED-digital counter). In the present study, the duration of a single PVT trial comprised 10 min. Sleepiness was also rated with this device before and after the reaction time task with the use of a 10-point scale.

Treatments

Participants received three drinks containing: 1) 36.4 mg cocoa polyphenols (control), 2) 469.3 mg cocoa polyphenols (medium CP), 3) 902.2 mg polyphenols (high CP) on separate occasions. In each case the treatment was made up of two sachets of powder mixed with 200 ml hot water. The control treatment consisted of 2 sachets of control CP, the 469.3 mg dose consisted of one control sachet plus one high CP sachet, and the 902.2 mg dose consisted of 2 high CP sachets. Nutritional information for the 2 sachets can be found in Tables 3-5 of Example 2. Five minutes was allowed for drink consumption.

Each participant was required to attend a total of four study days that were conducted not less than 3 days apart to ensure a sufficient wash out between conditions. Testing took place in a suite of laboratories with participants visually isolated from each other. On arrival at their first session on the first day participants were randomly allocated to a treatment regime using a Latin square design which counterbalanced the order of treatments across the three active days of the study. The first day involved completion of the test battery four times. This was undertaken in order to control for practice effects and to allow familiarization with the test battery and procedure on subsequent visits. The practice day data were not included in any analyses.

Each of the three active study days comprised four identical testing sessions. The first was a pre-dose testing session, which established baseline performance for that day. This was followed immediately by ingestion of that day's treatment. Further testing sessions began at 90 minutes, 3 hours and 6 hours following consumption of the day's treatment. Each testing session lasted approximately 30 minutes and comprised completion of the CDR test battery, Bond-Lader visual analogue mood scales, 10-minute PVT and production of a saliva sample with the use of a salivette. In addition, the pre-dose session and the 90 minute post-dose session also involved the taking of a 2 ml venous plasma sample prior to completion of the CDR battery.

Salivary caffeine levels were analysed to assess compliance to caffeine abstinence.

Prior to the primary statistical analysis separate, one way, repeated measures ANOVAS of pre-dose baseline data were conducted to ascertain any chance baseline differences in performance prior to the treatments.

Scores on the individual task outcomes were analysed as 'change from baseline' using SPSS 12.0.1.

The data from each measure were analysed by two-way repeated measures ANOVA [time (1.5, 3 and 6 hours post-dose)×treatment (469.3 mg CP/902.2 mg CP/control)].
Results Mean pre-dose baseline, and change from baseline scores for each measure for each condition were determined along with F-values and probabilities for effects of treatment.

Prior to analysis of change from baseline data, mean pre-dose raw baseline scores for all three conditions (control, 469.3 mg CP, 902.2 mg CP) for each outcome measure were subjected to a one-way, repeated-measures ANOVA. There were no significant baseline differences for any measure.

Salivary analysis confirmed adherence to caffeine abstinence instructions with mean baseline caffeine values of 0.79 µg/ml (levels just below 1 µg/ml have been reported for overnight caffeine abstinence-Evans and Griffith, 1999, Caffeine withdrawal: a parametric analysis of caffeine dosing conditions. *The Journal of Pharmacology and Experimental Therapeutics* 289:285-294). Analysis of post-treatment salivary caffeine levels revealed no significant differences between treatment conditions.
Post-Treatment Scores There were no significant post-treatment differences for any measure.

The tasks which make up the CDR assessment battery are wide-ranging in the abilities they measure but they are simple tasks which do not require a lot of effort. The results from this study show no effect of the compounds of the invention during performance of mentally non-demanding tasks.

What is claimed is:

1. A method of enhancing executive cognitive function in a subject comprising administering to the subject a composition comprising an effective amount of a component selected from the group consisting of one or more of the following: epicatechin, a pharmaceutically acceptable salt of epicatechun, at least one compound having the formula A, and pharmaceutically acceptable salts thereof:

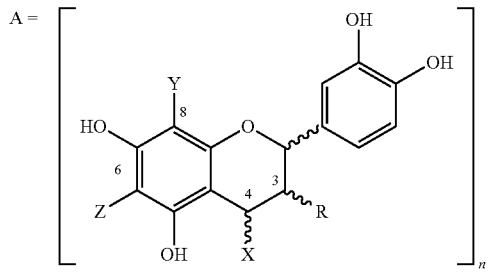

wherein
  n is an integer from 2 to 18;
  X has either α or β stereochemistry;
  R has α stereochemistry and is OH;
  the substituents of C-4, C-6 and C-8 are X, Z and Y, respectively, and bonding of monomeric units occurs at C-4, C-6 or C-8; and
  when any C-4, C-6 or C-8 is not bonded to another monomeric unit, X, Y and Z are hydrogen.

2. The method of claim 1, wherein the effective amount is at least 50 mg per unit dose and/or serving of the component.

3. The method of claim 2, wherein the subject is a human.

4. The method of claim 3, wherein the effective amount is at least 100 mg per unit dose and/or serving of the compound.

5. The method of claim 3, wherein the effective amount is 150 mg to 200 mg per unit dose and/or serving of the compound.

6. The method of claim 1, wherein the effective amount is at least 300 mg per day of the component.

7. The method of claim 6, wherein the effective amount is at least about 500 mg per day.

8. The method of claim 7, wherein the effective amount is at least about 900 mg per day.

9. The method of claim 3, wherein the composition is a pharmaceutical composition.

10. The method of claim 6, wherein the composition is selected from the group consisting of a food, a beverage, a confectionary, a cocoa extract, and a cocoa ingredient.

11. A method of increasing blood flow in brain vasculature in a subject comprising administering to the subject a composition comprising an effective amount of a component selected from the group consisting of one or more of the following: epicatechin, a pharmaceutically acceptable salt of epicatechin, at least one compound having the formula A, and pharmaceutically acceptable salts thereof:

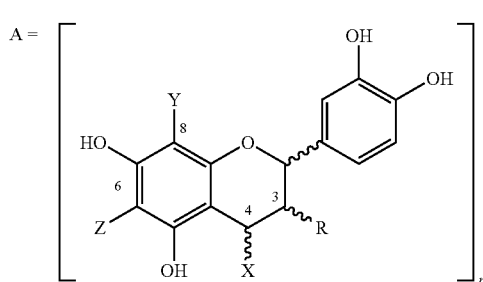

wherein
n is an integer from 2 to 18;
X has either α or β stereochemistry;
R has α stereochemistry and is OH;
the substituents of C-4, C-6 and C-8 are X, Z and Y, respectively, and bonding of monomeric units occurs at C-4, C-6 or C-8; and
when any C-4, C-6 or C-8 is not bonded to another monomeric unit, X, Y and Z are hydrogen.

12. The method of claim 11, wherein the effective amount is at least 50 mg per unit dose and/or serving of the component.

13. The method of claim 12, wherein the effective amount is at least 100 mg per unit dose and/or serving of the compound.

14. The method of claim 12, wherein the subject is a human.

15. The method of claim 14, wherein n is 2.

16. The method of claim 14, wherein the composition is selected from the group consisting of a food, a beverage, a confectionary, a cocoa extract, and a cocoa ingredient.

17. The method of claim 11, wherein the effective amount is at least 300 mg per day of the component.

18. The method of claim 17, wherein the effective amount is at least about 500 mg per day of the component.

19. The method of claim 17, wherein the composition is a packaged product with a label and/or instructions for use by the subject.

20. The method of claim 17, wherein the composition is selected from the group consisting of a food, a beverage, a confectionary, a cocoa extract, and a cocoa ingredient.

* * * * *